(12) United States Patent
Batycky et al.

(10) Patent No.: US 8,268,358 B2
(45) Date of Patent: *Sep. 18, 2012

(54) USE OF SIMPLE AMINO ACIDS TO FORM POROUS PARTICLES

(75) Inventors: Richard P. Batycky, Newton, MA (US); Michael M. Lipp, Framingham, MA (US); Ralph W. Niven, Half Moon Bay, CA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/010,032

(22) Filed: Jan. 20, 2011

(65) Prior Publication Data

US 2012/0020887 A1    Jan. 26, 2012

Related U.S. Application Data

(63) Continuation of application No. 11/637,353, filed on Dec. 12, 2006, now abandoned, which is a continuation of application No. 09/644,320, filed on Aug. 23, 2000, now Pat. No. 7,252,840, which is a continuation-in-part of application No. 09/382,959, filed on Aug. 25, 1999, now Pat. No. 6,586,008.

(51) Int. Cl.
*A61K 9/16* (2006.01)
*A61K 9/12* (2006.01)

(52) U.S. Cl. .......... 424/489; 424/46; 424/498; 424/502; 424/1.29; 424/9.1

(58) Field of Classification Search .................. 424/434, 424/450, 489–502, 43–46, 1.29, 9.1; 514/2, 514/3, 11
See application file for complete search history.

(56) References Cited

U.S. PATENT DOCUMENTS 5,985,309 A * 11/1999 Edwards et al. .............. 424/426
5,997,848 A * 12/1999 Patton et al. .................... 424/46

FOREIGN PATENT DOCUMENTS

WO    96/32096    * 10/1996

* cited by examiner

*Primary Examiner* — Gollamudi Kishore
(74) *Attorney, Agent, or Firm* — Elmore Patent Law Group, P.C.; Carolyn S. Elmore, Esq.; Darlene A Vanstone, Esq.

(57) ABSTRACT

Particles having a tap density of less than 0.4 g/cm$^3$ include a hydrophobic amino acid or salt thereof and a therapeutic, prophylactic or diagnostic agent or any combination thereof. Preferred particles include a phospholipid, have a median geometric diameter between about 5 and about 30 microns and an aerodynamic diameter between about 1 and about 5 microns. The particles can be formed by spray-drying and are useful for delivery to the pulmonary system.

15 Claims, No Drawings

USE OF SIMPLE AMINO ACIDS TO FORM POROUS PARTICLES

RELATED APPLICATIONS

This application is a continuation of U.S. application Ser. No. 11/637,353, filed Dec. 12, 2006, which is a continuation of U.S. application Ser. No. 09/644,320, filed Aug. 23, 2000, now U.S. Pat. No. 7,252,840, issued Aug. 7, 2007, which is a continuation-in-part of U.S. patent application Ser. No. 09/382,959, filed Aug. 25, 1999, now U.S. Pat. No. 6,586,008, issued Jul. 1, 2003. The entire teachings of the above application(s) are incorporated herein by reference.

BACKGROUND OF THE INVENTION

Aerosols for the delivery of therapeutic agents to the respiratory tract have been described, for example, Adjei, A. and Garren, J. *Pharm. Res.*, 7: 565-569 (1990); and Zanen, P. and Lamm, J.-W. J. *Int. J. Pharm.*, 114: 111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems*, 6: 273-313 (1990). The deep lung, or alveoli, are the primary target of inhaled therapeutic aerosols for systemic drug delivery.

Inhaled aerosols have been used for the treatment of local lung disorders including asthma and cystic fibrosis (Anderson, *Am. Rev. Respir. Dis.*, 140: 1317-1324 (1989)) and have potential for the systemic delivery of peptides and proteins as well (Patton and Platz, *Advanced Drug Delivery Reviews*, 8: 179-196 (1992)). However, pulmonary drug delivery strategies present many difficulties for the delivery of macromolecules; these include protein denaturation during aerosolization, excessive loss of inhaled drug in the oropharyngeal cavity (often exceeding 80%), poor control over the site of deposition, lack of reproducibility of therapeutic results owing to variations in breathing patterns, the frequent too-rapid absorption of drug potentially resulting in local toxic effects, and phagocytosis by lung macrophages.

Considerable attention has been devoted to the design of therapeutic aerosol inhalers to improve the efficiency of inhalation therapies. Timsina et. al., *Int. J. Pharm.*, 101: 1-13 (1995); and Tansey, I. P., *Spray Technol. Market*, 4: 26-29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., *J. Aerosol Sci.*, 27: 769-783 (1996). Dry powder formulations ("DPFs") with large particle size have improved flowability characteristics, such as less aggregation (Visser, J., *Powder Technology*, 58: 1-10 (1989)), easier aerosolization, and potentially less phagocytosis. Rudt, S. and R. H. Muller, *J. Controlled Release*, 22: 263-272 (1992); Tabata, Y. and Y. Ikada, *J. Biomed. Mater. Res.*, 22: 837-858 (1988). Dry powder aerosols for inhalation therapy are generally produced with mean geometric diameters primarily in the range of less than 5 μm. Ganderton, D., *J. Biopharmaceutical Sciences*, 3: 101-105 (1992); and Gonda, I. "Physico-Chemical Principles in Aerosol Delivery," in *Topics in Pharmaceutical Sciences 1991*, Crommelin, D. J. and K. K. Midha, Eds., Medpharm Scientific Publishers, Stuttgart, pp. 95-115, 1992. Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.*, 27: 769-783 (1996).

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. Pavia, D. "Lung Mucociliary Clearance," in *Aerosols and the Lung: Clinical and Experimental Aspects*, Clarke, S. W. and Pavia, D., Eds., Butterworths, London, 1984. Anderson, *Am. Rev. Respir. Dis.*, 140: 1317-1324 (1989). In the deep lungs, alveolar macrophages are capable of phagocytosing particles soon after their deposition. Warheit, M. B. and Hartsky, M. A., *Microscopy Res. Tech.*, 26: 412-422 (1993); Brain, J. D., "Physiology and Pathophysiology of Pulmonary Macrophages," in *The Reticuloendothelial System*, S. M. Reichard and J. Filkins, Eds., Plenum, New York, pp. 315-327, 1985; Dorries, A. M. and Valberg, P. A., *Am. Rev. Resp. Disease* 146: 831-837 (1991); and Gehr, P., *Microscopy Res. and Tech.*, 26: 423-436 (1993). As the diameter of particles exceeds 3 μm, there is increasingly less phagocytosis by macrophages. Kawaguchi, H., *Biomaterials*, 7: 61-66 (1986); Krenis, L. J. and Strauss, B., *Proc. Soc. Exp. Med.*, 107: 748-750 (1961); and Rudt, S. and Muller, R. H., *J. Contr. Rel.*, 22: 263-272 (1992). However, increasing the particle size also has been found to minimize the probability of particles (possessing standard mass density) entering the airways and acini due to excessive deposition in the oropharyngeal or nasal regions. Heyder, J., *J. Aerosol Sci.*, 17: 811-825 (1986).

Local and systemic inhalation therapies can often benefit from a relatively slow controlled release of the therapeutic agent. Gonda, I., "Physico-chemical principles in aerosol delivery," in: *Topics in Pharmaceutical Sciences 1991*, D. J. A. Crommelin and K. K. Midha, Eds., Stuttgart: Medpharm Scientific Publishers, pp. 95-117 (1992). Slow release from a therapeutic aerosol can prolong the residence of an administered drug in the airways or acini, and diminish the rate of drug appearance in the bloodstream. Also, patient compliance is increased by reducing the frequency of dosing. Langer, R., *Science*, 249: 1527-1533 (1990); and Gonda, I., "Aerosols for delivery of therapeutic and diagnostic agents to the respiratory tract," in *Critical Reviews in Therapeutic Drug Carrier Systems* 6: 273-313 (1990).

Controlled release drug delivery to the lung may simplify the way in which many drugs are taken. Gonda, I., *Adv. Drug Del. Rev.*, 5: 1-9 (1990); and Zeng, X., et al., *Int. J. Pharm.*, 124: 149-164 (1995). Pulmonary drug delivery is an attractive alternative to oral, transdermal, and parenteral administration because self-administration is simple, the lungs provide a large mucosal surface for drug absorption, there is no first-pass liver effect of absorbed drugs, and there is reduced enzymatic activity and pH mediated drug degradation compared with the oral route. Relatively high bioavailability of many molecules, including macromolecules, can be achieved via inhalation. Wall, D. A., *Drug Delivery*, 2: 1-20 1995); Patton, J. and Platz, R., *Adv. Drug Del. Rev.*, 8: 179-196 (1992); and Byron, P., *Adv. Drug. Del. Rev.*, 5: 107-132 (1990). As a result, several aerosol formulations of therapeutic drugs are in use or are being tested for delivery to the lung. Patton, J. S., et al., *J. Controlled Release*, 28: 79-85 (1994); Damms, B. and Bains, W., *Nature Biotechnology* (1996); Niven, R. W., et al., *Pharm. Res.*, 12(9): 1343-1349 (1995); and Kobayashi, S., et al., *Pharm. Res.*, 13(1): 80-83 (1996).

Drugs currently administered by inhalation come primarily as liquid aerosol formulations. However, many drugs and excipients, especially proteins, peptides (Liu, R., et al., *Biotechnol. Bioeng.*, 37: 177-184 (1991)), and biodegradable carriers such as poly(lactide-co-glycolides) (PLGA), are unstable in aqueous environments for extended periods of time. This can make storage as a liquid formulation problematic. In addition, protein denaturation can occur during aerosolization with liquid formulations. Mumenthaler, M., et al., *Pharm. Res.*, 11: 12-20 (1994). Considering these and other limitations, dry powder formulations (DPF's) are gaining increased interest as aerosol formulations for pulmonary delivery. Damms, B. and W. Bains, *Nature Biotechnology* (1996); Kobayashi, S., et al., *Pharm. Res.*, 13(1): 80-83 (1996); and Timsina, M., et al., *Int. J. Pharm.*, 101: 1-13 (1994). However, among the disadvantages of DPF's is that powders of ultrafine particulates usually have poor flowability and aerosolization properties, leading to relatively low respirable fractions of aerosol, which are the fractions of inhaled aerosol that escape deposition in the mouth and throat. Gonda, I., in *Topics in Pharmaceutical Sciences* 1991, D. Crommelin and K. Midha, Editors, Stuttgart: Medpharm Scientific Publishers, 95-117 (1992). A primary concern with many aerosols is particulate aggregation caused by particle-particle interactions, such as hydrophobic, electrostatic, and capillary interactions.

An effective dry-powder inhalation therapy for both short and long term release of therapeutics, either for local or systemic delivery, requires a powder that displays minimum aggregation, as well as a means of avoiding or suspending the lung's natural clearance mechanisms until drugs have been effectively delivered.

One formulation for dry powder pulmonary delivery involves the separation of active particles from a carrier on actuation of the inhaler. Due to blending requirements, preparing these powders is associated with an increased number of steps. Furthermore, the method of delivery of these powders is associated with several disadvantages. For example, there are inefficiencies in the release of active particles from the carrier. Moreover, the carrier takes up significantly more volume than the active particle, thus high drug doses are difficult to achieve. In addition, the large lactose particles can impact the back of the throat, causing coughing.

Therefore, a need exists for dry-powders suitable for inhalation which minimize or eliminate the above-mentioned problems.

SUMMARY OF THE INVENTION

The invention relates to particles having a tap density of less than about 0.4 $g/cm^3$. The particles include an amino acid or a salt thereof. In one embodiment, the particles include a therapeutic, prophylactic or diagnostic agent or any combination thereof. In another embodiment, the particles include a phospholipid. In still another embodiment, the particles have a median geometric diameter of between about 5 micrometers and about 30 micrometers. In a further embodiment, the particles have an aerodynamic diameter of between about 1 and about 5 microns.

The invention also relates to a method of producing particles having a tap density of less than about 0.4 $g/cm^3$. The method includes forming a mixture which includes a therapeutic, prophylactic or diagnostic agent, or any combination thereof, and an amino acid or a salt thereof and spray-drying the mixture to form particles having a tap density of less than about 0.4 $g/cm^3$. In one embodiment of the invention, the mixture includes a phospholipid. In other embodiments, the mixture includes an organic solvent or an organic-aqueous co-solvent.

The invention further relates to a method for drug delivery to the pulmonary system. The method includes administering to the respiratory tract of a patient in need of treatment, prophylaxis or diagnosis an effective amount of particles having a tap density of less than about 0.4 $g/cm^3$. The particles include a therapeutic, prophylactic or diagnostic agent, or any combination thereof, and an amino acid or salt thereof. In one embodiment, the particles include a phospholipid. In another embodiment, delivery to the respiratory system includes delivery to the deep lung. In still another embodiment of the invention, delivery to the respiratory system includes delivery to the central airways. In a further embodiment of the invention, delivery to the respiratory system includes delivery to the upper airways.

The invention relates also to a composition for drug delivery to the pulmonary system. The composition includes particles which incorporate a therapeutic, prophylactic or diagnostic agent and an amino acid or salt thereof and which have a tap density of less than about 0.4 $g/cm^3$.

Preferred amino acids include hydrophobic amino acids. Examples include but are not limited to leucine, isoleucine, alanine, valine and phenylalanine Other amino acids that can be employed are amino acids which are insoluble in the solvent system employed to form the particles.

Preferred phospholipids include but are not limited to phosphatidic acid, phosphatidylcholines, phosphatidylethanolamines, phosphatidylglycerols, phosphatidylserines, phosphatidylinositols and combinations thereof.

The invention has several advantages. For example, the particles of the invention incorporate amino acids which, in the amounts that are administered to the respiratory system of a patient, are expected to be non-toxic. Furthermore, amino acids are relatively inexpensive thus lowering overall particle manufacturing costs. Still further, the invention is capable of conferring extended release properties as well as improved formulability. In contrast to methods in which active particles are released from the carrier on actuation of the inhaler, the entire particles of the invention go to the desired site of the pulmonary system. Drugs can be delivered in higher doses and with higher efficiency. Lodging of particle material in the back of the throat is avoided. The method of forming particles can be carried out using simple, inexpensive solvents which do not raise emission and solvent recovery concerns. The method permits the use of Class 3 or better solvents. Furthermore, the method requires less process steps than methods employed to form powders which release active particles from the carrier upon actuation of the inhaler.

DETAILED DESCRIPTION OF THE INVENTION

The features and other details of the invention, either as steps of the invention or as combination of parts of the invention, will now be more particularly described and pointed out in the claims. It will be understood that the particular embodiments of the invention are shown by way of illustration and not as limitations of the invention. The principle feature of this invention may be employed in various embodiments without departing from the scope of the invention.

The invention is directed to particles having a tap density of less than about 0.4 $g/cm^3$ which include an amino acid or a salt thereof and methods of producing such particles. The invention is also directed to methods of delivering the particles to the pulmonary system of a patient.

In a preferred embodiment the amino acid is hydrophobic. Suitable hydrophobic amino acids include naturally occurring and non-naturally occurring hydrophobic amino acids. Non-naturally occurring amino acids include, for example, beta-amino acids, Both D, L configurations and racemic mixtures of hydrophobic amino acids can be employed. Suitable hydrophobic amino acids can also include amino acid derivatives or analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

In a preferred embodiment of the invention, the amino acid is insoluble in the solvent system employed, such as, for example, in a 70:30 (vol/vol) ethanol:water co-solvent.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10% weight. Preferably, the amino acid salt is present in the particles in an amount ranging from about 20 to about 80 weight %.

Examples of therapeutic, prophylactic or diagnostic agents include synthetic inorganic and organic compounds, proteins, peptides, polypeptides, polysaccharides and other sugars, lipids, and DNA and RNA nucleic acid sequences having therapeutic, prophylactic or diagnostic activities. Nucleic acid sequences include genes, antisense molecules which bind to complementary DNA or RNA and inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Compounds with a wide range of molecular weight can be encapsulated, for example, between 100 and 500,000 grams or more per mole.

The particles can include a therapeutic agent for local delivery within the lung, such as agents for the treatment of asthma, chronic obstructive pulmonary disease (COPD), emphysema, or cystic fibrosis, or for systemic treatment. For example, genes for the treatment of diseases such as cystic fibrosis can be administered, as can beta agonists steroids, anticholinergics and leukotriene modifiers for asthma. Other specific therapeutic agents include, but are not limited to, human growth hormone, insulin, calcitonin, gonadotropin-releasing hormone ("LHRH"), granulocyte colony-stimulating factor ("G-CSF"), parathyroid hormone-related peptide, somatostatin, testosterone, progesterone, estradiol, nicotine, fentanyl, norethisterone, clonidine, scopolamine, salicylate, cromolyn sodium, salmeterol, formoterol, albuterol, and Valium.

Any of a variety of diagnostic agents can be incorporated within the particles, which can locally or systemically deliver the incorporated agents following administration to a patient. Biocompatible or pharmacologically acceptable gases can be incorporated into the particles or trapped in the pores of the particles using technology known to those skilled in the art. The term gas refers to any compound which is a gas or capable of forming a gas at the temperature at which imaging is being performed. In one embodiment, retention of gas in the particles is improved by forming a gas-impermeable barrier around the particles. Such barriers are well known to those of skill in the art.

Diagnostic agents also include but are not limited to imaging agents which include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include but are not limited to the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

The particles of the invention can also be precursors to tablet formulations.

Preferably, a therapeutic, prophylactic, diagnostic agent or a combination thereof can be present in the spray-dried particles in an amount ranging from less than about 1 weight % to about 90 weight %.

In another embodiment of the invention, the particles include a phospholipid, also referred to herein as phosphoglyceride. In a preferred embodiment, the phospholipid, is endogenous to the lung. In another preferred embodiment the phospholipid includes, among others, phosphatidic acid, phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof.

The phospholipid, can be present in the particles in an amount ranging from about 0 to about 90 weight %. Preferably, it can be present in the particles in an amount ranging from about 10 to about 60 weight %.

Suitable methods of preparing and administering particles which include phospholipids, are described in U.S. Pat. No. 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety.

In still another embodiment of the invention the particles include a surfactant such as, but not limited to the phospholipids described above. Other surfactants, such as, for example, hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); tyloxapol can also be employed.

As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

The surfactant can be present in the particles in an amount ranging from about 0 to about 90 weight %. Preferably, it can be present in the particles in an amount ranging from about 10 to about 60 weight %.

The a preferred embodiment of the invention, the particles include a therapeutic, prophylactic or diagnostic agent, or combinations thereof, a hydrophobic amino acid or a salt thereof, and a phospholipid.

In one embodiment of the invention, the phospholipid or combination or phospholipids present in the particles can have a therapeutic, prophylactic or diagnostic role. For example, the particles of the invention can be used to deliver surfactants to the lung of a patient. This is particularly useful in medical indications which require supplementing or replacing endogenous lung surfactants, for example in the case of infant respiratory distress syndrome.

The particles of the invention can have desired drug release properties. In one embodiment, the particles include one or more phospholipids selected according to their transition temperature. For example, by administering particles which include a phospholipid or combination of phospholipids which have a phase transition temperature higher than the patient's body temperature, the release of the therapeutic, prophylactic or diagnostic agent can be slowed down. On the other hand, rapid release can be obtained by including in the particles phospholipids having low transition temperatures. Particles having controlled release properties and methods of modulating release of a biologically active agent are described in U.S Provisional Application 60/150,742, filed on Aug. 25, 1999, and U.S. patent application Ser. No. 09/644,736, entitled "Modulation of Release From Dry Powder Formulations;" the contents of both are incorporated herein by reference in their entirety.

Particles, and in particular particles having controlled or sustained release properties, also can include other materials. For example, the particles can include a biocompatible, and preferably biodegradable polymer, copolymer, or blend. Such polymers are described, for example, in U.S. Pat. No. 5,874,064, issued on Feb. 23, 1999 to Edwards et al., the teachings of which are incorporated herein by reference in their entirety. Preferred polymers are those which are capable of forming aerodynamically light particles having a tap density less than about 0.4 g/cm$^3$, a mean diameter between about 5 µm and about 30 µm and an aerodynamic diameter between approximately one and five microns, preferably between about one and about three microns. The polymers can be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides can be used to form the particles. For example, polyanhydrides such as poly[(p-carboxyphenoxy)-hexane anhydride] (PCPH) may be used. Suitable biodegradable polyanhydrides are described in U.S. Pat. No. 4,857,311.

In another embodiment, bulk eroding polymers such as those based on polyesters including poly(hydroxy acids) can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(D,L-lactic-co-glycolic acid) ("PLGA") which incorporate a phospholipid such as DPPC.

Still other polymers include but are not limited to polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

In one embodiment, the particles include functionalized polyester graft copolymers, as described in Hrkach et al., *Macromolecules*, 28: 4736-4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications*, ACS Symposium Series No. 627, Raphael M. Ottenbrite et al., Eds., American Chemical Society, Chapter 8, pp. 93-101, 1996.

Materials other than biodegradable polymers can be included in the spray-dried particles of the invention. Suitable materials include various non-biodegradable polymers and various excipients. Examples of excipients include, but are not limited to: a sugar, such as lactose, polysaccharides, cyclodextrins and/or a surfactant.

In yet another embodiment of the invention, the particles also include a carboxylate moiety and a multivalent metal salt. Such compositions are described in U.S Provisional Application 60/150,662, filed on Aug. 25, 1999, and U.S. patent application Ser. No. 09/644,105, entitled "Formulation for Spray-Drying Large Porous Particles," the teachings of both are incorporated herein by reference in their entirety. In a preferred embodiment, the particles include sodium citrate and calcium chloride.

The particles of the invention can be employed in compositions suitable for drug delivery to the pulmonary system. For example, such compositions can include the particles and a pharmaceutically acceptable carrier for administration to a patient, preferably for administration via inhalation. The particles can be co-delivered, for example, with larger carrier particles, not carrying a therapeutic agent, having, for example, a mean diameter ranging between about 50 μm and about 100 μm.

The particles of the invention have a tap density less than about 0.4 g/cm$^3$. As used herein, the phrase "aerodynamically light particles" refers to particles having a tap density less than about 0.4 g/cm$^3$. Particles having a tap density of less than about 0.1 g/cm$^3$ are preferred. The tap density of particles of a dry powder can be obtained using a GEOPYC™ instrument (Micrometrics Instrument Corp., Norcross, Ga. 30093). A Dual Platform Microprocessor Controlled Tap Density Tester (Vankel, N.C.) can also be used. Tap density is a standard measure of the envelope mass density. The envelope mass density of an isotropic particle is defined as the mass of the particle divided by the minimum sphere envelope volume within which it can be enclosed. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure.

Aerodynamically light particles have a preferred size, e.g., a volume median geometric diameter (VMGD) of at least about 5 microns (μm). In one embodiment, the VMGD is from about 5 μm to about 30 μm. In another embodiment of the invention, the particles have a VMGD ranging from about 10 μm to about 30 μm. In other embodiments, the particles have a median diameter, mass median diameter (MMD), a mass median envelope diameter (MMED) or a mass median geometric diameter (MMGD) of at least 5 μm, for example from about 5 μm and about 30 μm.

The diameter of the particles, for example, their MMGD or their VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition within targeted sites within the respiratory tract.

Aerodynamically light particles preferably have "mass median aerodynamic diameter" (MMAD), also referred to herein as "aerodynamic diameter", between about 1 μm and about 5 μm. In one embodiment of the invention, the MMAD is between about 1 μm and about 3 μm. In another embodiment, the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

Process conditions as well as efficiency of inhaler, in particular with respect to dispersibility, can contribute to the size of particles that can be delivered to the pulmonary system.

Aerodynamically light particles may be fabricated or separated, for example by filtration or centrifugation, to provide a particle sample with a preselected size distribution. For example, greater than about 30%, 50%, 70%, or 80% of the particles in a sample can have a diameter within a selected range of at least about 5 μm. The selected range within which a certain percentage of the particles must fall may be for example, between about 5 and about 30 μm, or optimally between about 5 and about 15 μm. In one preferred embodiment, at least a portion of the particles have a diameter between about 9 and about 11 μm. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 μm.

Aerodynamically light particles with a tap density less than about 0.4 g/cm$^3$, median diameters of at least about 5 μm, and an aerodynamic diameter of between about 1 and about 5 μm, preferably between about 1 and about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials* 7: 61-66 (1986); Krenis, L. J. and Strauss, B., *Proc. Soc. Exp. Med.,* 107: 748-750 (1961); and Rudt, S. and Muller, R. H., *J. Contr. Rel.,* 22: 263-272 (1992). For particles of statistically isotropic shape, such as spheres with rough surfaces, the particle envelope volume is approximately equivalent to the volume of cytosolic space required within a macrophage for complete particle phagocytosis.

Aerodynamically light particles thus are capable of a longer term release of an encapsulated agent in the lungs. Following inhalation, aerodynamically light biodegradable particles can deposit in the lungs, and subsequently undergo slow degradation and drug release, without the majority of the particles being phagocytosed by alveolar macrophages. The drug can be delivered relatively slowly into the alveolar fluid, and at a controlled rate into the blood stream, minimizing possible toxic responses of exposed cells to an excessively high concentration of the drug. The aerodynamically light particles thus are highly suitable for inhalation therapies, particularly in controlled release applications.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.,* 26: 293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95-117, Stuttgart: Medpharm Scientific Publishers, 1992)), by the formula:

$$d_{aer} = d\sqrt{\rho}$$

where the envelope mass ρ is in units of g/cm³. Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.,* 17: 811-825 (1986). Due to their small envelope mass density, the actual diameter d of aerodynamically light particles comprising a monodisperse inhaled powder that will exhibit maximum deep-lung deposition is:

$$d = 3/\sqrt{\rho} \; \mu m \; (\text{where } \rho < 1 \; g/cm^3);$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology,* 58: 1-10. Thus, large particle size increases efficiency of aerosolization to the deep lung for particles of low envelope mass density, in addition to contributing to lower phagocytic losses.

In one embodiment of the invention, the spray-dried particles have a tap density less than about 0.4 g/cm³ and a median diameter between about 5 μm and about 30 μm, which in combination yield an aerodynamic diameter of between about 1 and about 5 μm, and for delivery to the deep lung, preferably between about 1 and about 3 μm. The aerodynamic diameter is calculated to provide for maximum deposition within the lungs, previously achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

In another embodiment of the invention, the particles have a mass density of less than about 0.4 g/cm³ and a mean diameter of between about 5 μm and about 30 μm. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm³ and a mean diameter of between about 5 μm and about 30 μm is between about 1 μm and about 5 μm.

The invention also relates to methods of preparing particles having a tap density less than about 0.4 g/cm³. In one embodiment, the method includes forming a mixture including a therapeutic, prophylactic or diagnostic agent, or a combination thereof, and an amino acid or a salt thereof. The therapeutic, prophylactic or diagnostic agents which can be employed include but are not limited to those described above. The amino acids or salts thereof, include but are not limited to those described before.

In a preferred embodiment, the mixture includes a surfactant, such as, for example, the surfactants described above. In another preferred embodiment, the mixture includes a phospholipid, such as, for example the phospholipids described above. An organic solvent or an aqueous-organic solvent can be employed to form the mixture.

Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others.

Co-solvents that can be employed include an aqueous solvent and an organic solvent, such as, but not limited to, the organic solvents as described above. Aqueous solvents include water and buffered solutions. In one embodiment, an ethanol water solvent is preferred with the ethanol:water ratio ranging from about 50:50 to about 90:10 ethanol:water.

The mixture can have a neutral, acidic or alkaline pH. Optionally, a pH buffer can be added to the solvent or co-solvent or to the formed mixture. Preferably, the pH can range from about 3 to about 10.

The mixture is spray-dried. Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed.

In a preferred embodiment, a rotary atomizer is employed. An example of suitable spray driers using rotary atomization includes the Mobile Minor spray drier, manufactured by Niro, Denmark. The hot gas can be, for example, air, nitrogen or argon.

Preferably, the particles of the invention are obtained by spray drying using an inlet temperature between about 100° C. and about 400° C. and an outlet temperature between about 50° C. and about 130° C.

Without being held to any particular theory, it is believed that due to their hydrophobicity and low water solubility, hydrophobic amino acids facilitate the formation of a shell during the drying process when an ethanol:water co-solvent is employed. It is also believed that the amino acids may alter the phase behavior of the phospholipids in such a way as to facilitate the formation of a shell during the drying process.

The particles of the invention can be used for delivery to the pulmonary system. They can be used to provide controlled systemic or local delivery of therapeutic or diagnostic agents to the respiratory tract via aerosolization. Administration of the particles to the lung by aerosolization permits deep lung delivery of relatively large diameter therapeutic aerosols, for example, greater than about 5 µm in median diameter. The particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass median diameters for example in the range between about 50 µm and about 100 µm.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6: 273-313, 1990; and in Moren, "Aerosol dosage forms and formulations," in: *Aerosols in Medicine. Principles, Diagnosis and Therapy*, Moren, et al., Eds, Esevier, Amsterdam, 1985.

The use of biodegradable polymers permits controlled release in the lungs and long-time local action or systemic bioavailability. Denaturation of macromolecular drugs can be minimized during aerosolization since macromolecules can be contained and protected within a polymeric shell. Coencapsulation of peptides with peptidase-inhibitors can minimize peptide enzymatic degradation. Pulmonary delivery advantageously can reduce or eliminate the need for injection. For example, the requirement for daily insulin injections can be avoided.

The invention is also related to a method for drug delivery to the pulmonary system. The method comprises administering to the respiratory tract of a patient in need of treatment, prophylaxis or diagnosis an effective amount of particles comprising a therapeutic, prophylactic or diagnostic agent and a hydrophobic amino acid. In a preferred embodiment, the particles include a phospholipid. As used herein, the term "effective amount" means the amount needed to achieve the desired effect or efficacy.

Porous or aerodynamically light particles, having a geometric size (or mean diameter) in the range of about 5 to about 30 µm, and tap density less than about 0.4 g/cm$^3$, such that they possess an aerodynamic diameter of about 1 and about 3 µm, have been shown to display ideal properties for delivery to the deep lung. Larger aerodynamic diameters, ranging, for example, from about 3 to about 5 µm are preferred, however, for delivery to the central and upper airways. According to one embodiment of the invention the particles have a tap density of less than about 0.4 g/cm$^3$ and a mean diameter of between about 5 µm and about 30 µm. According to another embodiment of the invention, the particles have a mass density of less than about 0.4 g/cm$^3$ and a mean diameter of between about 5 µm and about 30 µm. In one embodiment of the invention, the particles have an aerodynamic diameter between about 1 µm and about 5 µm. In another embodiment of the invention, the particles have an aerodynamic diameter between about 1 µm and about 3 µm microns. In still another embodiment of the invention, the particles have an aerodynamic diameter between about 3 µm and about 5 µm.

Particles including a medicament, for example one or more of the drugs listed above, are administered to the respiratory tract of a patient in need of treatment, prophylaxis or diagnosis. Administration of particles to the respiratory system can be by means such as known in the art. For example, particles are delivered from an inhalation device. In a preferred embodiment, particles are administered via a dry powder inhaler (DPI). Metered-dose-inhalers (MDI), nebulizers or instillation techniques also can be employed.

Such devices are known in the art. For example, a DPI is described in U.S. Pat. No. 4,069,819 issued on Aug. 5, 1976 and U.S. Pat. No. 4,995,385, issued on Feb. 26, 1991, both to Valentini, et al. Examples of other suitable inhalers are described in U.S. Pat. No. 5,997,848 issued Dec. 7, 1999 to Patton, et al. Various other suitable devices and methods of inhalation which can be used to administer particles to a patient's respiratory tract are known in the art. Examples include, but are not limited to, the Spinhaler® (Fisons, Loughborough, U.K.), ROTAHALER® (Glaxo-Wellcome, Research Triangle Technology Park, N.C.), FLOWCAPS® (Hovione, Loures, Portugal), Inhalator® (Boehringer-Ingelheim, Germany), and the AEROLIZER® (Novartis, Switzerland), DISKHALER® (Glaxo-Wellcome, RTP, NC) and others, such as known to those skilled in the art. Preferably, the particles are administered as a dry powder via a dry powder inhaler.

In one embodiment of the invention, delivery to the pulmonary system of particles is in a single, breath-actuated step, as described in U.S. patent application, entitled "High Efficient Delivery of a Large Therapeutic Mass Aerosol," application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

The present invention will be further understood by reference to the following non-limiting examples.

EXEMPLIFICATIONS

Some of the methods and materials employed in the following examples are described in U.S. application Ser. No. 09/211,940, filed Dec. 15, 1998, in U.S. application Ser. No. 08/739,308, filed Oct. 29, 1996, now U.S. Pat. No. 5,874,064, in U.S. application Ser. No. 08/655,570, filed May 24, 1996, in U.S. application Ser. No. 09/194,068, filed May 23, 1997, in PCT/US97/08895 application filed May 23, 1997, in U.S. application Ser. 08/971,791, filed Nov. 17, 1997, in U.S. application Ser. No. 08/784,421, filed Jan. 16, 1997, now U.S. Pat. No. 5,855,913 and in U.S. application Ser. No. 09/337,245, filed on Jun. 22, 1999, all of which are incorporated herein by reference in their entirety.

Materials

Leucine was obtained from Spectrum Chemical Company. DPPC was obtained from Avanti Polar Lipids (Alabaster, Ala.).

Spray Drying

A Mobile Minor spray-drier from Niro was used. The gas employed was dehumidified air. The gas temperature ranged from about 80 to about 150° C. The atomizer speed ranged from about 15,000 to about 50,000 RPM. The gas rate was 70 to 92 kg/hour and the liquid feed rate ranged from about 50 to about 100 ml/minute.

Geometric Size Distribution Analysis

Size distributions were determined using a Coulter Multisizer II. Approximately 5-10 mg of powder was added to 50 mL isoton II solution until the coincidence of particles was between 5 and 8%. Greater than 500,000 particles were counted for each batch of spheres.

Aerodynamic Size Distribution Analysis

Aerodynamic size distribution was determined using an Aerosizer/Aerodisperser (Amherst Process Instruments, Amherst, Mass.). Approximately 2 mg powder was introduced into the Aerodisperser and the Aerodynamic size was determined by time of flight measurements.

Example 1

A mixture including 40 weight % of an amino acid and 60 weight % DPPC was formed in a 70/30 vol/vol ethanol-water co-solvent and spray-dried. The results are shown in Table 1.

Table 1 shows median geometric and aerodynamic diameters for particles including several amino acids, their hydrophobicity and estimated tap density. Tap density was estimated using the equation discussed above.

TABLE 1

| Amino acid | hydrophobicity | MMGD | MMAD | Est. tap density |
|---|---|---|---|---|
| Leucine | 0.943 | 7.9 | 3.0 | 0.11 |
| Isoleucine | 0.943 | 8.1 | 2.7 | 0.14 |
| Phenylalanine | 0.501 | 7.9 | 3.8 | 0.23 |
| Glutamine | 0.251 | 6.5 | 4.4 | 0.45 |
| Glutamate | 0.043 | 5.1 | 4.1 | 0.64 |

Example 2

Mixtures including 60 weight % DPPC with varying ratios of leucine and lactose were formed in a 70/30 vol/vol ethanol-water cosolvent and spray-dried. The mixtures included: (A) 60:40 DPPC:leucine, (B) 60:20:20 DPPC:leucine:lactose and (C) 60:40 DPPC:lactose. The spray-drying operating conditions were held constant for each of the runs (these included an inlet temperature of 100° C., an atomizer spin rate of 20,000 RPM, a fluid feed rate of 65 ml/min and a dewpoint in the range of −15 to −20° C.). The results are shown in Table 2. In summary, the replacement of leucine with increasing amounts of lactose led to a reduction in yield and particle geometric size, and an increase in particle MMAD and density. Increasing amounts of lactose also appeared to lead to an increase in the tendency of the particles to agglomerate.

TABLE 2

| Formulations | yield (%) | MMGD (μm) | MMAD (μm) | Est. Tap. Density g/cm$^3$ |
|---|---|---|---|---|
| A | 27 | 8.04 | 2.97 | 0.14 |
| B | 26 | 6.54 | 3.67 | 0.31 |
| C | 1 | 4.70 | 3.85 | 0.67 |

Example 3

Particles containing albuterol sulfate were prepared in the following manner. A mixture including 76% DSPC, 20% leucine and 4% albuterol sulfate was formed in a 70/30 (v/v) ethanol/water co-solvent and spray dried. The mass median geometric diameter of the resulting particles was 8.2 μm and the mass median aerodynamic diameter was 2.8 μm.

Example 4

Particles including 4% albuterol sulfate, 60% DPPC and 36% leucine, alanine or glycine were formed as described above. A comparison of the characteristics of each set of particles is shown in Table 3. For each formulation the table shows the amino acid employed, the mass median aerodynamic diameter (MMAD), the volumetric median geometric diameter (VMGD), and the density calculated using the equation $d_{aer}=d_g*\sqrt{\rho}$. The data show that all three amino acids were useful in forming particles suitable for pulmonary delivery. Leucine and alanine formulations appeared best suited for delivery which is preferentially to the deep lung while glycine formulations appeared more suitable for delivery that is preferential to the central and upper airways.

TABLE 3

| Formulations | Amino acid (36% w/w) | MMAD (μm) | VMGD (μm) | Calculated Density g/cm$^3$ |
|---|---|---|---|---|
| A | leucine | 2.38 | 10.28 | 0.054 |
| B | alanine | 3.17 | 11.48 | 0.076 |
| C | glycine | 5.35 | 13.09 | 0.167 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing particles having a tap density less than 0.4 g/cm$^3$ comprising:
    (a) forming a mixture including a therapeutic, prophylactic or diagnostic agent, or any combination thereof, and an amino acid or a salt thereof; and (b) spray-drying said mixture to produce particles having a tap density less than about 0.4 $g/cm^3$.

2. The method of claim 1, wherein the particles have a median geometric diameter of between about 5 micrometers and about 30 micrometers.

3. The method of claim 1, wherein the particles have an aerodynamic diameter of between about 1 and about 5 microns.

4. The method of claim 3, wherein the particles have an aerodynamic diameter of between about 1 and about 3 microns.

5. The method of claim 3, wherein the particles have an aerodynamic diameter of between about 3 and 5 microns.

6. The method of claim 1, wherein the amino acid is hydrophobic.

7. The method of claim 6, wherein the hydrophobic amino acid is selected form the group consisting of leucine, isoleucine, alanine, valine, phenylalanine and any combination thereof.

8. The method of claim 3, wherein the hydrophobic amino acid is present in the particles in an amount of at least 10% weight.

9. The method of claim 1, wherein the therapeutic, prophylactic or diagnostic agent is present in the particles in an amount ranging from about 1 to about 90% weight.

10. The method of claim 1, wherein the particles further comprise a surfactant.

11. The method of claim 1, wherein the particles further comprise a phospholipid.

12. The method of claim 11, wherein the phospholipid is endogenous to the lung.

13. The method of claim 11, wherein the phospholipid is selected from the group consisting of phosphatidylcholines, phosphatidylethanolamines, phosphatidylglycerols, phosphatidylserines, phosphatidylinositols and combinations thereof.

14. The method of claim 1, wherein the mixture comprises an organic solvent.

15. The method of claim 1, wherein the mixture comprises a co-solvent including an organic solvent and an aqueous solvent.

* * * * *